United States Patent
Houck et al.

(10) Patent No.: US 12,223,026 B2
(45) Date of Patent: Feb. 11, 2025

(54) USER DEVICE INCORPORATING MULTI-SENSING SENSOR DEVICE

(71) Applicant: VIAVI Solutions Inc., Chandler, AZ (US)

(72) Inventors: William D. Houck, Santa Rosa, CA (US); Markus Bilger, Santa Rosa, CA (US)

(73) Assignee: VIAVI Solutions Inc., Chandler, AZ (US)

( * ) Notice: Subject to any disclaimer, the term of this patent is extended or adjusted under 35 U.S.C. 154(b) by 0 days.

(21) Appl. No.: 18/147,089

(22) Filed: Dec. 28, 2022

(65) Prior Publication Data

US 2023/0161856 A1 May 25, 2023

Related U.S. Application Data (63) Continuation of application No. 16/365,316, filed on Mar. 26, 2019, now Pat. No. 11,562,053.
(Continued)

(51) Int. Cl.
*G06F 21/32* (2013.01)
*A61B 5/021* (2006.01)
(Continued)

(52) U.S. Cl.
CPC .............. *G06F 21/32* (2013.01); *A61B 5/021* (2013.01); *A61B 5/02444* (2013.01); *G01N 21/25* (2013.01); *G06F 1/1626* (2013.01)

(58) Field of Classification Search
CPC ... H04W 12/06; H04W 12/065; H04W 12/65; H04W 12/68; H04W 88/02; H04W 12/12;
(Continued)

(56) References Cited

U.S. PATENT DOCUMENTS

| 8,300,897 B2 | 10/2012 | Nagasaka et al. |
| 10,275,585 B2 | 4/2019 | Fadell et al. |

(Continued)

FOREIGN PATENT DOCUMENTS

| EP | 3435123 A1 | 1/2019 |
| JP | 2006051279 A | 2/2006 |

(Continued)

OTHER PUBLICATIONS

Demichelis F., et al., "Optical Properties of Hydrogenated Amorphous Silicon", Journal of Applied Physics, Jan. 15, 1986, vol. 59 (2), pp. 611-618, XP055643758.
(Continued)

*Primary Examiner* — Kwasi Karikari
(74) *Attorney, Agent, or Firm* — Harrity & Harrity, LLP (57) ABSTRACT

A device may include a sensor window. The sensor window may include a substrate. The sensor window may include a set of layers disposed onto the substrate. The set of layers may include a first subset of layers of a first refractive index and a second set of layers of a second refractive index different from the first refractive index. The set of layers may be associated with a threshold transmissivity in a sensing spectral range, and may be configured to a particular color in a visible spectral range and associated with a threshold opacity in the visible spectral range. The device may include a spectral sensor device aligned to the sensor window and including at least one sensor element to receive light in the sensing spectral range and provide a plurality of sensing functionalities based on at least one measurement of the light in the sensing spectral range.

20 Claims, 6 Drawing Sheets

Related U.S. Application Data (60) Provisional application No. 62/678,014, filed on May 30, 2018.

(51) Int. Cl.
  *A61B 5/024* (2006.01)
  *G01N 21/25* (2006.01)
  *G06F 1/16* (2006.01)

(58) Field of Classification Search
  CPC ... H04W 12/062; H04W 12/08; H04W 12/77; H04W 12/0433; H04W 4/029; H04W 12/02; H04W 12/03; H04W 12/33; H04W 12/72
  See application file for complete search history.

(56) References Cited

U.S. PATENT DOCUMENTS

| | | |
|---|---|---|
| 10,694,982 B2 | 6/2020 | Kobayashi et al. |
| 2012/0257031 A1 | 10/2012 | Tsuchiya et al. |
| 2015/0205992 A1 | 7/2015 | Rowe |
| 2016/0026884 A1* | 1/2016 | Ferren .................. G03B 3/00 382/118 |
| 2017/0135586 A1 | 5/2017 | Jeon et al. |
| 2017/0337412 A1* | 11/2017 | Bhat .................. A61B 5/1172 |
| 2017/0357840 A1 | 12/2017 | Chen et al. |
| 2018/0067245 A1 | 3/2018 | Giachino et al. |
| 2019/0370447 A1 | 12/2019 | Houck et al. |

FOREIGN PATENT DOCUMENTS

| | | |
|---|---|---|
| JP | 2009093385 A | 4/2009 |
| JP | 2012217571 A | 11/2012 |
| JP | 2012221141 A | 11/2012 |
| JP | 2012254194 A | 12/2012 |
| JP | 2015167022 A | 9/2015 |
| JP | 2017196319 A | 11/2017 |
| WO | 2017132360 A1 | 8/2017 |

OTHER PUBLICATIONS

Extended European Search Report for Application No. EP19176626.0, mailed on Mar. 11, 2020, 11 pages.
Partial European Search Report for Application No. EP19176626.0, mailed on Nov. 28, 2019, 14 pages.
Rowe R.K., et al., "Multispectral Fingerprint Image Acquisition," Advances in Biometrics, 2008, 20 pages.
Rowe R.K., et al., "Multispectral Fingerprint Image Acquisition," Advances in Biometrics, White Paper, 2008, 16 pages.

* cited by examiner

USER DEVICE INCORPORATING MULTI-SENSING SENSOR DEVICE

RELATED APPLICATION(S)

This application is a continuation of U.S. patent application Ser. No. 16/365,316, filed Mar. 26, 2019, which claims priority under 35 U.S.C. § 119 to U.S. Provisional Patent Application No. 62/678,014, filed on May 30, 2018, the contents of each of which are incorporated by reference herein in their entireties.

BACKGROUND

A user device may include a camera. For example, a user device may include a camera that captures images of an object, of a user, and/or the like. The user device may also include one or more other types of sensor devices. For example, some user devices may include a fingerprint reader to determine an identity of a user and to perform a security function. Similarly, some user devices may include a heart rate monitor to measure a pulse of the user and to perform a health function. Some user devices may connect to external peripherals to perform one or more functions. For example, a user device may connect to an external heart rate monitor worn by a user to enable the external heart rate monitor to monitor a pulse of the user. Similarly, external peripherals may be used to monitor blood oxygenation, to perform fingerprint scanning, and/or the like for a user device.

SUMMARY

According to some possible implementations, a device may include a sensor window. The sensor window may include a substrate. The sensor window may include a set of layers disposed onto the substrate. The set of layers may include a first subset of layers of a first refractive index and a second set of layers of a second refractive index different from the first refractive index. The set of layers may be associated with a threshold transmissivity in a sensing spectral range, and may be configured to a particular color in a visible spectral range and associated with a threshold opacity in the visible spectral range. The device may include a spectral sensor device aligned to the sensor window and including at least one sensor element to receive light in the sensing spectral range and provide a plurality of sensing functionalities based on at least one measurement of the light in the sensing spectral range.

According to some possible implementations, an optical device may include a plurality of sensor elements. The optical device may include a plurality of layers. The plurality of layers may include a set of high refractive index layers associated with a first refractive index and a set of low refractive index layers associated with a second refractive index that is less than the first refractive index. The plurality of layers may form a plurality of channels to direct a plurality of wavelengths of light. The plurality of layers may be associated with a threshold transmissivity in a sensing spectral range and a threshold opacity in a visible spectral range. The plurality of sensor elements may be aligned to the plurality of channels and configured to perform a health parameter monitoring determination and a biometric identification determination based on measurements of the plurality of wavelengths of light.

According to some possible implementations, a sensor device may include a sensor element array including a plurality of sensor elements. The sensor element array may be configured to perform a plurality of measurements of a plurality of wavelengths of light. The sensor element array may be configured to provide information identifying a plurality of characteristics of an object based on the plurality of measurements. The sensor device may include a multispectral filter including a set of high refractive index layers and low refractive index layers. The multispectral filter may be configured to direct the plurality of wavelengths of light to the sensor element array.

DETAILED DESCRIPTION

The following detailed description of example implementations refers to the accompanying drawings. The same reference numbers in different drawings may identify the same or similar elements.

A user device may include sensor devices to perform sensing functionalities. An optical transmitter, of a sensor device, may emit light that is directed toward an object. For example, in an object detection system, the optical transmitter may transmit near-infrared light toward an object, and the near-infrared light may be reflected off the object toward the sensor device. An optical receiver of a sensor device, such as a sensor element array, may receive light that is directed toward the sensor device. For example, in the object detection system, a sensor element array may capture information about one or more wavelengths of light. The sensor element array may include a set of sensor elements (e.g., optical sensors, spectral sensors, and/or image sensors) that capture the information about the one or more wavelengths of light. In this way, based on the information about the one or more wavelengths of light, the sensor device may detect an object.

Similarly, information captured by an optical receiver of a sensor device may be used to recognize a characteristic of an object. For example, the sensor device may utilize information regarding wavelengths of light reflected off an object to determine a distance to the object, a size of the object, a shape of the object, a spectroscopic signature of the object, a type of the object, a speed of the object, and/or the like. Similarly, the sensor device may determine an identity of a person, a characteristic of the person (e.g., a height, a weight, a speed of movement, a health characteristic, and/or the like), and/or the like.

Some user devices, such as mobile phones, wearable devices (e.g., a smart wristwatch or a pair of smart eyeglasses), and/or the like, may include multiple sensor devices to perform multiple sensing functionalities. For example, a user device may include a camera to capture an image, a fingerprint reader to provide a fingerprint identification functionality, and/or the like. Similarly, the user device may connect to external peripherals to provide functionalities, such as connecting to an external heart rate monitor to provide a health parameter monitoring functionality. However, including multiple, discrete sensor devices in a user device may result in excessive cost, excessive package size, excessive utilization of power resources, and/or excessive utilization of processing resources. Moreover, connecting to an external peripheral may result in excessive cost and/or package size to provide connectivity functionalities, excessive traffic via a network connection, and/or the like.

Some implementations described herein may provide a user device incorporating a multi-sensing sensor device. For example, the user device may include a multispectral filter and a sensor device that provides sensing for a plurality of functionalities, such as performing one or more health monitoring functionalities, one or more security functionalities, and/or the like. In this way, the user device may be associated with a reduced package size, a reduced cost, a reduced utilization of power resources, a reduced utilization of network resources, and/or the like relative to incorporating multiple, discrete single-functionality sensor devices and/or connecting to multiple external peripherals.

Figure 1A:
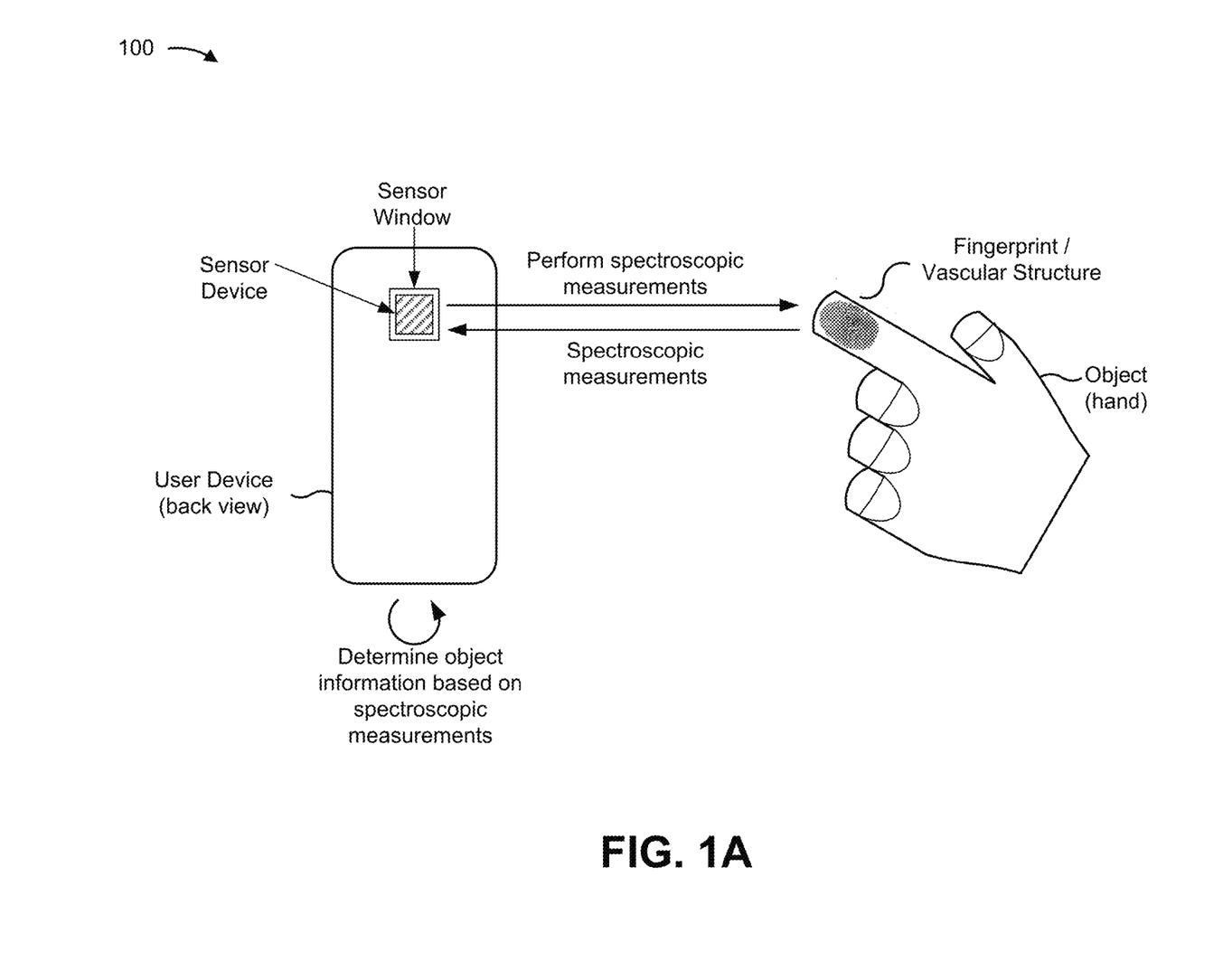
FIGS. 1A and 1B are diagrams of an example implementation described herein.
Figure 1B:
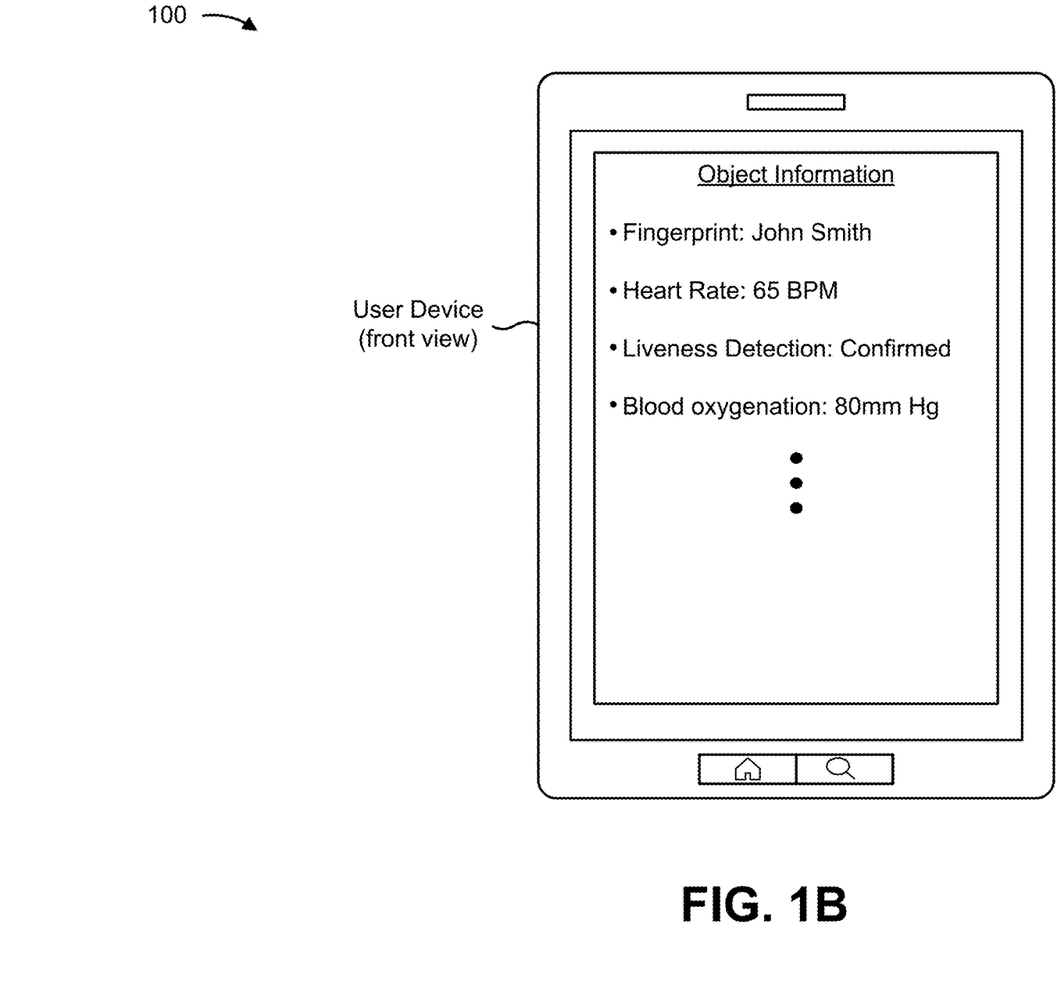

FIGS. 1A and 1B are diagrams of an example implementation 100 described herein. As shown in FIG. 1A, example 100 may include a user device including a sensor device and a sensor window. In some implementations, the sensor window may be opaque in a visible spectral range and transmissive in a sensing spectral range (e.g., a near-infrared spectral range, a mid-infrared spectral range, and/or the like). In some implementations, the sensor window may be configured to be a particular color in the visible spectral range to match an adjacent surface of the user device to conceal the sensor device. In some implementations, the sensor window may protect the sensor device from an external environment, thereby improving durability of the sensor device relative to providing an exposed sensor device.

As further shown in FIG. 1A, the sensor device may transmit light to perform a spectroscopic measurement, and may receive reflected light to enable the spectroscopic measurements. In some implementations, the sensor device may determine a biometric authentication based on a tissue structure in a finger (e.g., based on receiving light reflected off capillaries and/or veins in the finger and determining the vascular structure in the finger). For example, the sensor device may transmit near-infrared light through the sensor window to enable subcutaneous biometric authentication (e.g., identification of a tissue structure of the finger or another body part). In this case, based on using a subcutaneous identification technique (e.g., sensing to a penetration depth of greater than approximately 0.1 microns, greater than approximately 0.5 microns, greater than approximately 1 micron, greater than approximately 3 microns, greater than approximately 5 microns, and/or the like), the sensor device improves an accuracy of biometric authentication relative to surface-based fingerprint identification techniques, which may be hindered by surface damage to a finger, dirt on the finger, water on the finger, and/or the like.

Additionally, or alternatively, the sensor device may transmit the near-infrared light to enable a heart rate determination. For example, the sensor device may transmit near-infrared light toward the user's hand, may receive reflected light, and may detect a pulse of the user based on measurements of one or more wavelengths of the reflected light. Based on the heart rate determination, the sensor device may determine a liveness of an object. For example, the sensor device may distinguish between an artificial imprint of a fingerprint or tissue structure and a fingerprint or tissue structure on an actual, living person, thereby improving a security of a biometric authentication functionality. In some implementations, the sensor device may perform another determination, such as a blood oxygenation determination, a blood sugar level determination, and/or the like based on measurements of one or more wavelengths of reflected light. Additionally, or alternatively, the sensor device may perform a spectroscopic classification, quantification, and/or the like using measurements of near-infrared light. In this way, by using surface measurements and subsurface measurements, the sensor device improves sensing for the user device.

As shown in FIG. 1B, the user device may provide, via a user interface, object information based on the sensor device performing measurements (e.g., spectroscopic measurements). For example, the sensor device may provide information identifying a user based on a fingerprint, information identifying a heart rate, information indicating that a fingerprint was from a person and not an artificial imprint, information identifying a blood oxygenation level, and/or the like via the user interface. In some implementations, the user device may perform a response action based on the sensor determination. For example, the user device may automatically unlock a user interface of the user device based on a biometric authentication and a liveness determination. Additionally, or alternatively, the user device may automatically alter a layout of a screen and/or one or more preferences of the user device based on user stored preferences and based on identifying the user using a biometric authentication and a liveness determination. Additionally, or alternatively, the user device may automatically transmit an alert (e.g., to an emergency response dispatch device) identifying the user, identifying a location of the user, and indicating a health condition based on a biometric authentication and one or more health metrics (e.g., a heart rate determination, a blood oxygenation determination, a blood sugar level determination, and/or the like).

In this way, based on using a single sensor device to perform, for example, a biometric authentication and a heart rate determination, the user device may be associated with a reduced size, reduced cost, reduced complexity, reduced utilization of power resources, reduced utilization of network, and/or the like relative to a user device with multiple, discrete, single-functionality sensor devices.

As indicated above, FIGS. 1A and 1B are provided merely as one or more examples. Other examples may differ from what is described with regard to FIGS. 1A and 1B.

Figure 2:
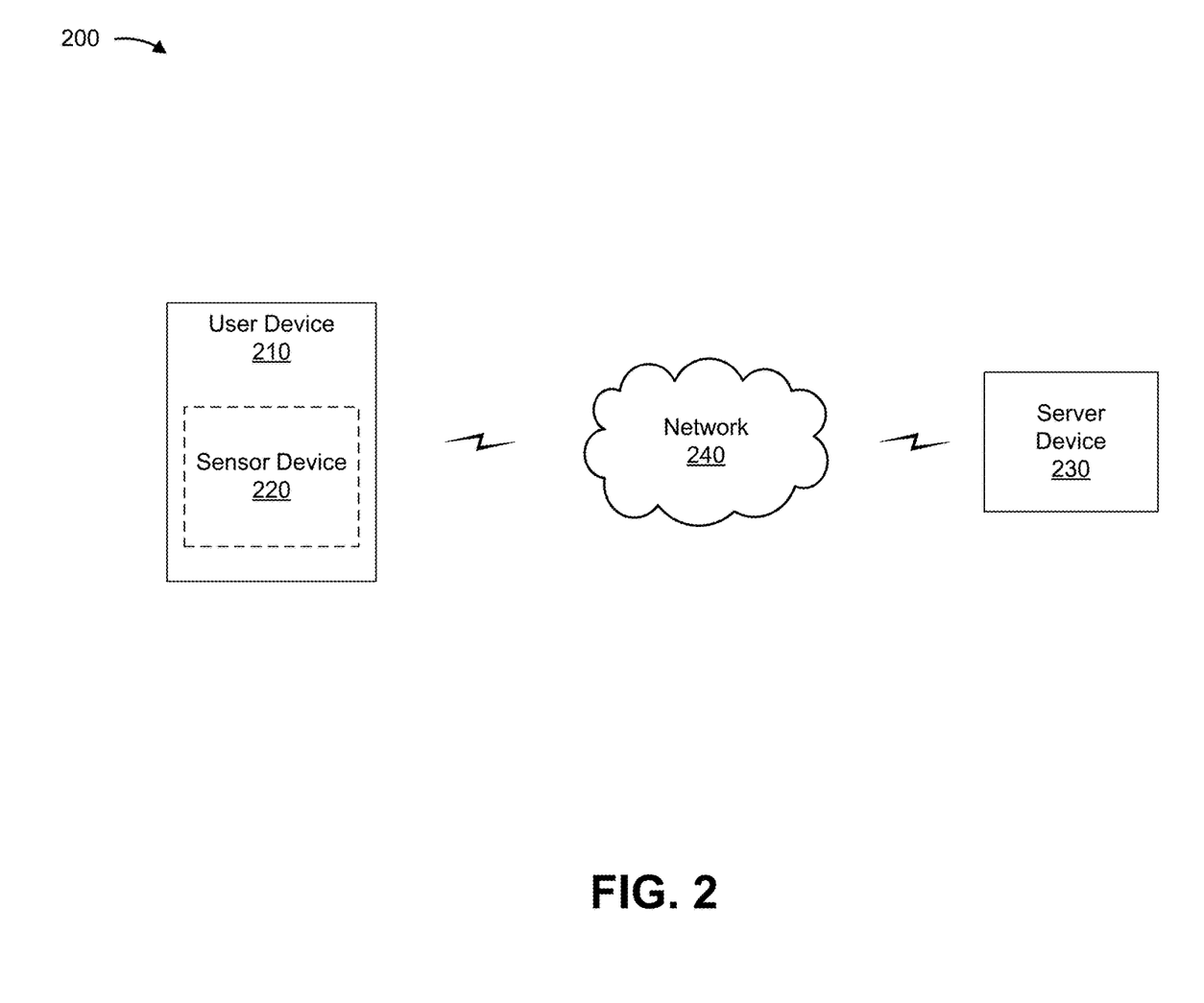
FIG. 2 is a diagram of an example environment in which systems and/or methods described herein may be implemented.

FIG. 2 is a diagram of an example environment 200 in which systems and/or methods described herein may be implemented. As shown in FIG. 2, environment 200 may include a user device 210, which includes a sensor device 220, a server device 230, and a network 240. Devices of environment 200 may interconnect via wired connections, wireless connections, or a combination of wired and wireless connections.

User device 210 includes one or more devices capable of receiving, generating, storing, processing, and/or providing information associated with a sensor determination. For example, user device 210 may include a communication and/or computing device, such as a mobile phone (e.g., a smart phone, a radiotelephone, and/or the like), a computer (e.g., a laptop computer, a tablet computer, a handheld computer, and/or the like), a gaming device, a wearable communication device (e.g., a smart wristwatch, a pair of smart eyeglasses, and/or the like), or a similar type of device. In some implementations, user device 210 may include a housing that houses sensor device 220. In some implementations, the housing may include a sensor window that separates sensor device 220 from an external environment. For example, the sensor window may be a multispectral filter to filter light, may be opaque at visible light wavelengths, may be transmissive at sensing wavelengths (e.g., near-infrared wavelengths, mid-infrared wavelengths, and/or the like), and/or the like. In some implementations, sensor device 220 may be disposed in user device 210 (e.g., on a back of user device 210, behind a display of user device 210, and/or the like). For example, when sensor device 220 is disposed behind the display of user device 210, the display of user device 210 may form a sensor window for user device 210. In some implementations, user device 210 may receive information from and/or transmit information to another device in environment 200, such as sensor device 220 and/or server device 230.

Sensor device 220 may include an optical device capable of storing, processing, and/or routing information associated with sensor determination and/or one or more devices capable of performing a sensor measurement on an object. For example, sensor device 220 may include a spectrometer device that performs spectroscopy (e.g., vibrational spectroscopy, such as a near infrared (NIR) spectrometer, a mid-infrared spectroscopy (mid-IR), Raman spectroscopy, and/or the like). In some implementations, sensor device 220 may perform multiple characteristic determinations for multiple characteristics of an object for user device 210, thereby obviating a need for user device 210 to include multiple sensor devices. For example, sensor device 220 may provide a health parameter monitoring determination, a biometric authentication determination, a liveness detection determination, a blood pressure determination, a blood oxygenation determination, and/or the like to user device 210, as described herein. In this case, sensor device 220 may utilize the same wavelengths, different wavelengths, a combination of the same wavelengths and different wavelengths, and/or the like for the multiple characteristic determinations.

In some implementations, sensor device 220 may be incorporated into user device 210, such as a wearable spectrometer and/or the like. In some implementations, sensor device 220 may generate a classification model based on a set of measurements of a training set, validate the classification model based on a set of measurements of a validation set, and/or utilize the classification model to perform spectroscopic classification or quantification based on a set of measurements of an unknown set (e.g., an object on which a sensor measurement is to be performed). In some implementations, sensor device 220 may include a sensor element array to perform measurements of multiple wavelengths of light for multiple sensing functionalities. In some implementations, sensor device 220 may receive information from and/or transmit information to another device in environment 200, such as user device 210 and/or server device 230.

Server device 230 includes one or more devices capable of storing, processing, and/or routing information associated with a sensor determination. For example, server device 230 may include a server that receives information identifying a spectroscopic measurement from user device 210, performs a determination regarding the spectroscopic measurement (e.g., determines a heart rate based on the spectroscopic measurement, an identification of a user based on the spectroscopic measurement, and/or the like), and provides information identifying the determination to user device 210. In some implementations, server device 230 may include a communication interface that allows server device 230 to receive information from and/or transmit information to other devices in environment 200.

Network 240 includes one or more wired and/or wireless networks. For example, network 240 may include a cellular network (e.g., a long-term evolution (LTE) network, a code division multiple access (CDMA) network, a 3G network, a 4G network, a 5G network, another type of next generation network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. For example, although sensor device 220 and user device 210 are described as separate devices, sensor device 220 and user device 210 may be implemented as a single device. Additionally, or alternatively, a set of devices (e.g., one or more devices) of environment 200 may perform one or more functions described as being performed by another set of devices of environment 200.

Figure 3:
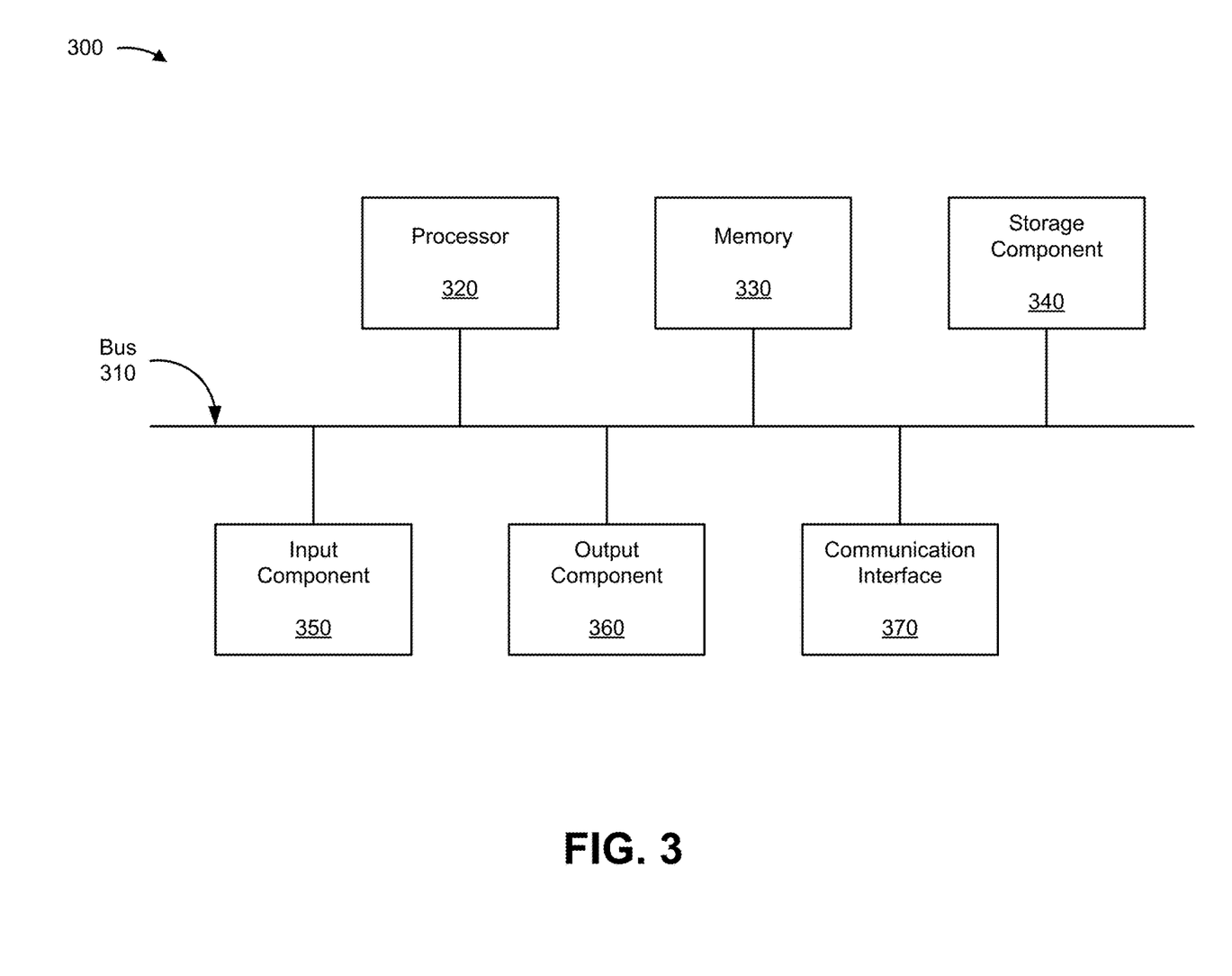
FIG. 3 is a diagram of example components of one or more devices of FIG. 2.

FIG. 3 is a diagram of example components of a device 300. Device 300 may correspond to user device 210, sensor device 220, and/or server device 230. In some implementations, user device 210, sensor device 220, and/or server device 230 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among multiple components of device 300. Processor 320 is implemented in hardware, firmware, and/or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RANI), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a multispectral sensor coupled to a multispectral filter, a sensor element array, a global positioning system (GPS) component, an accelerometer, a gyroscope, and/or an actuator). Output component 360 includes a component that provides output information from device 300 (e.g., a display, a speaker, and/or one or more light-emitting diodes (LEDs), an optical transmitter to transmit a near-infrared signal).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes based on processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardware circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
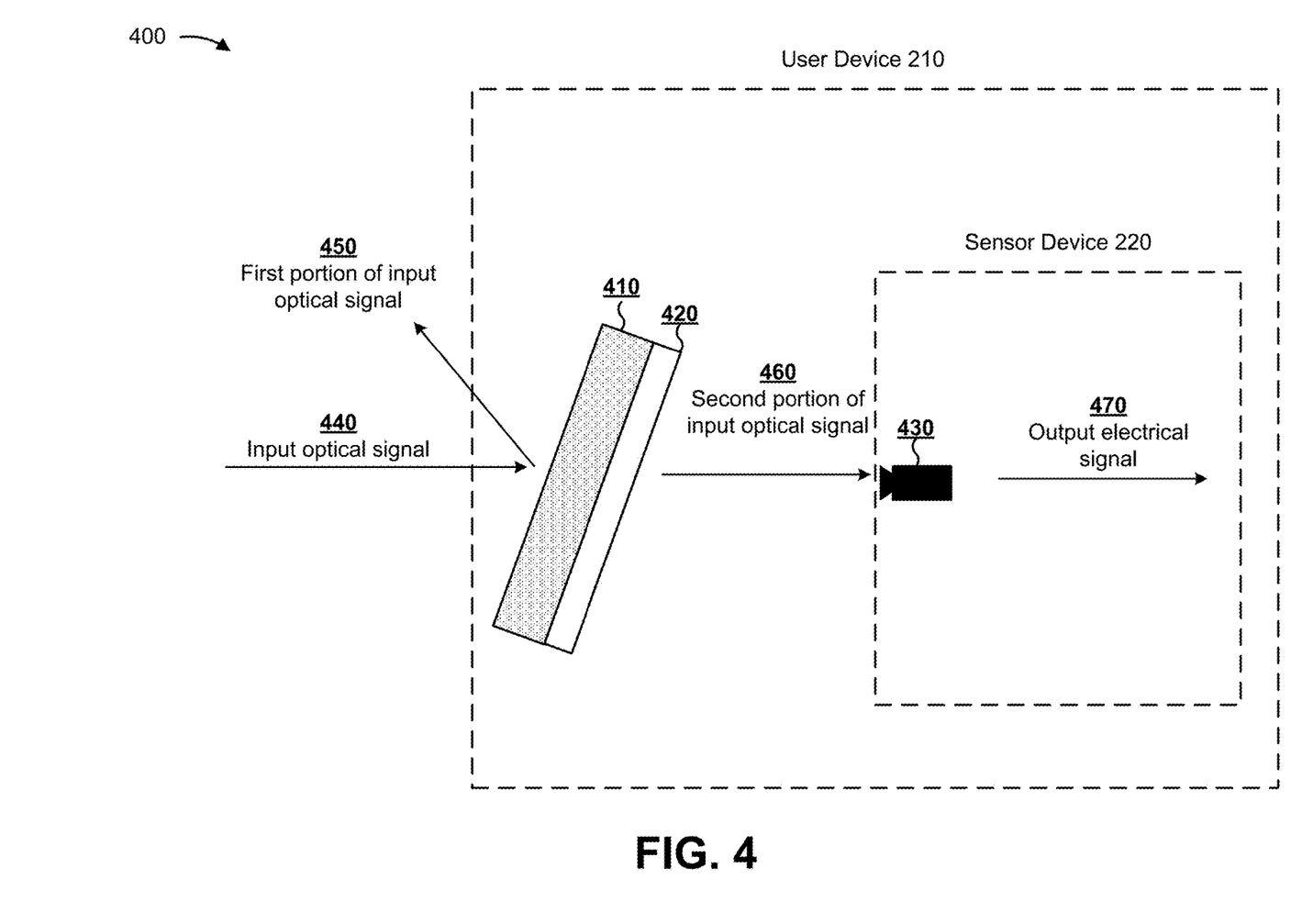
FIG. 4 is a diagram of an example implementation described herein.

FIG. 4 is a diagram of an example implementation 400 described herein. As shown in FIG. 4, example implementation 400 includes sensor device 220 incorporated into user device 210. User device 210 includes a sensor window 410, which is disposed on a substrate 420, and a sensor element array 430 of sensor device 220. In some implementations, sensor window 410 may be an optical filter that performs a filtering functionality. For example, sensor window 410 may include alternating high refractive index material layers and low refractive index material layers to provide color selectivity and to direct light to multiple sensor elements of sensor element array 430 associated with multiple wavelength channels.

As further shown in FIG. 4, and by reference number 440, an input optical signal is directed toward sensor window 410. The input optical signal may include but is not limited to light associated with a particular spectral range (e.g., a near-infrared spectral range, a mid-infrared spectral range, a visible spectral range, and/or the like). For example, an optical transmitter (e.g., of sensor device 220 and/or user device 210) may direct the light toward sensor element array 430 to permit sensor element array 430 to perform a measurement of the light (e.g., the optical transmitter may direct the light toward an object and the light may be reflected toward sensor element array 430). In some implementations, the input optical signal may be reflected ambient light directed toward sensor element array 430 (e.g., without a signal transmitted toward an object to cause light to be reflected toward sensor element array 430).

As further shown in FIG. 4, and by reference number 450, a first portion of the input optical signal with a first spectral range is not passed through by sensor window 410. For example, dielectric filter stacks of dielectric thin film layers, which may include high index material layers and low index material layers of sensor window 410, may cause the first portion of the input optical signal to be reflected in a first direction, to be absorbed, and/or the like. In some implementations, the first portion of the input optical signal may include first light that is reflected to cause sensor window 410 to appear to a viewer as opaque and/or with a particular color and second light that is absorbed. In some implementations, the first portion of the input optical signal may be a threshold portion of light incident on sensor window 410 not included in a bandpass of sensor window 410, such as greater than 95% of light, greater than 99% of light, and/or the like in a visible spectral range. Additionally, or alternatively, sensor window 410 may be transmissive in at least a part of the visible spectral range, such as to enable visible light imaging by sensor element array 430, thereby obviating a need for a separate camera in user device 210.

As further shown in FIG. 4, and by reference number 460, a second portion of the input optical signal is passed through by sensor window 410. For example, sensor window 410 may pass through the second portion of the input optical signal with a second spectral range in a second direction toward sensor element array 430. In this case, the second portion of the input optical signal may be a threshold portion of light incident on sensor window 410 within a bandpass of sensor window 410, such as greater than 50% of incident light, greater than 90% of light, greater than 95% of light, greater than 99% of light, and/or the like in a near-infrared spectral range. In some implementations, sensor window 410 may be associated with multiple component filters associated with multiple spectral ranges. For example, based on varying a thickness of sensor window 410 and/or a thickness of a subset of layers thereof, different portions of sensor window 410 may pass different wavelengths of light to different sensor elements of sensor element array 430, thereby enabling multispectral sensing.

As further shown in FIG. 4, and by reference number 470, based on the second portion of the input optical signal being passed to sensor element array 430, sensor element array 430 may provide an output electrical signal for sensor device 220, such as for use in identifying a fingerprint, determining a heart rate, imaging, ambient light sensing, detecting the presence of an object, identifying a person, performing a measurement, facilitating communication, and/or the like. In some implementations, another arrangement of sensor window 410 and sensor element array 430 may be utilized. For example, rather than passing the second portion of the input optical signal collinearly with the input optical signal, sensor window 410 may direct the second portion of the input optical signal in another direction toward a differently located sensor element array 430.

Although some implementations described herein are described in terms of a sensor element array, other types of sensor device 220 configurations may be possible, such as a set of discrete sensor elements or another type of optical sensor.

As indicated above, FIG. 4 is provided as an example. Other examples may differ from what is described with regard to FIG. 4.

Figure 5:
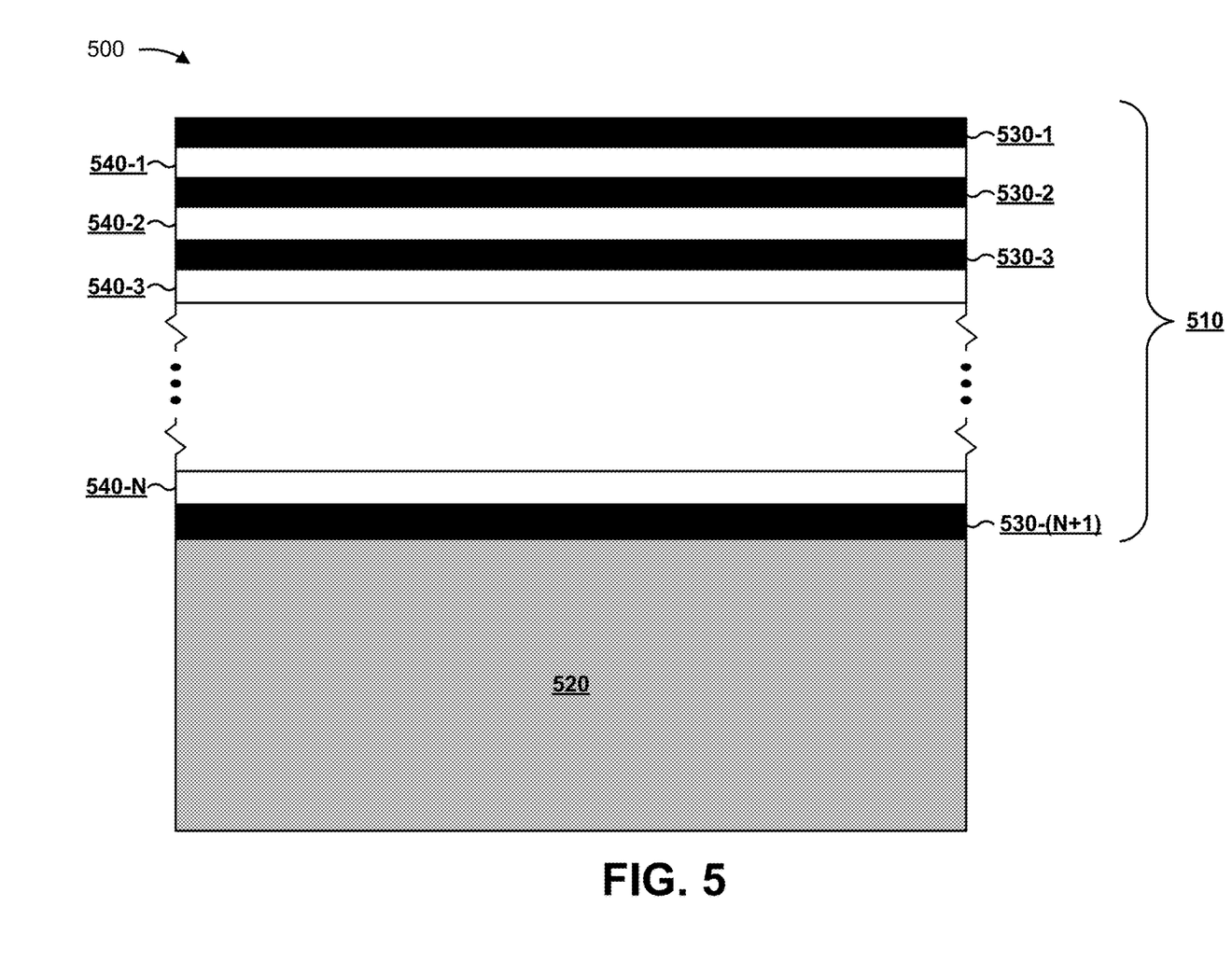
FIG. 5 is a diagram of an example implementation described herein.

FIG. 5 is a diagram of an example optical filter 500. FIG. 5 shows an example stackup of an optical filter described herein. As further shown in FIG. 5, optical filter 500 includes an optical filter coating portion 510 and a substrate 520. In some implementations, optical filter 500 may form a sensor window, such as sensor window 410 of FIG. 4.

Optical filter coating portion 510 includes a set of optical filter layers. For example, optical filter coating portion 510 includes a first set of layers 530-1 through 530-(N+1) (N≥1) and a second set of layers 540-1 through 540-N. In another example, optical filter coating portion 510 may be a single type of layer (e.g., one or more layers 530), three or more types of layers (e.g., one or more layers 530, one or more layers 540, and one or more of one or more other types of layers), and/or the like. In some implementations, optical filter coating portion 510 may be disposed on a single side of substrate 520, on multiple sides of substrate 520, and/or the like.

In some implementations, layers 530 may include a set of layers of a high refractive index material (H layers), such as silicon layers, hydrogenated silicon layers, silicon-germanium (SiGe) layers, hydrogenated germanium layers, hydrogenated silicon-germanium layers, and/or the like. In some implementations, layers 530 may be associated with a refractive index of greater than approximately 3.0, greater than approximately 3.5, greater than approximately 3.6, greater than approximately 3.8, greater than approximately 4.0, and/or the like. Although some layers may be described as a particular material, such as SiGe, some layers may include (small quantities of) phosphor, boron, nitride, hydrogen, a noble gas, and/or the like.

In some implementations, layers 540 may include a set of layers of a low refractive index material (L layers), such as silicon dioxide layers and/or the like. Additionally, or alternatively, the L layers may include tantalum pentoxide ($Ta_2O_5$) layers, niobium pentoxide ($Nb_2O_5$) layers, titanium dioxide ($TiO_2$) layers, aluminum oxide ($Al_2O_3$) layers, zirconium oxide ($ZrO_2$) layers, yttrium oxide ($Y_2O_3$) layers, silicon nitride ($Si_3N_4$) layers, magnesium fluoride ($MgF_2$) layers, niobium titanium fluoride (NbTiF) layers, niobium titanium oxide (NbTiO) layers, an anion/cation mixture layer, a combination thereof, and/or the like. In some implementations, layer 540 may be associated with a refractive index of less than approximately 2.5, less than approximately 2.0, less than approximately 1.5, and/or the like.

In some implementations, optical filter coating portion 510 may be associated with a particular quantity of layers, m. For example, an optical filter for use as a sensor window may include a quantity of alternating high refractive index layers and low refractive index layers, such as a range of 2 layers to 200 layers. In some implementations, optical filter coating portion 510 may be fabricated using a sputtering procedure. For example, optical filter coating portion 510 may be fabricated using a pulsed-magnetron based sputtering procedure to sputter alternating layers 530 and 540 on a glass substrate, a silica substrate, or another type of substrate. In some implementations, multiple cathodes may be used for the sputtering procedure, such as a first cathode to sputter silicon and a second cathode to sputter germanium, thereby forming a silicon-germanium layer. In some implementations, optical filter coating portion 510 may include one or more other types of layers to provide one or more other functionalities, such as a hydrophobic layer, an oleophobic layer, a protective layer (e.g., a coating disposed on top of optical filter coating portion 510), an anti-reflectance layer, an out of band blocker layer (e.g., to block a particular spectral range), and/or the like. In some implementations, substrate 520 may be chemically strengthened glass to provide protection to one or more sensor elements covered by substrate 520.

In some implementations, optical filter coating portion 510 may be annealed using one or more annealing procedures, such as a first annealing procedure at a temperature of approximately 280 degrees Celsius or between approximately 200 degrees Celsius and approximately 400 degrees Celsius, a second annealing procedure at a temperature of approximately 320 degrees Celsius or between approximately 250 degrees Celsius and approximately 350 degrees Celsius, and/or the like.

In some implementations, each layer of optical filter coating portion 510 may be associated with a particular thickness. For example, layers 530 and 540 may each be associated with a thickness of between 1 nm and 1500 nm, between 10 nm and 500 nm, and/or the like. Additionally, or alternatively, optical filter 500 may be associated with a thickness of between 100 μm and 5 millimeters (mm), less than approximately 3 mm, less than approximately 1 mm, and/or the like. In some implementations, at least one of layers 530 and 540 may each be associated with a thickness of less than 1000 nm, less than 100 nm, or less than 5 nm, and/or the like. Additionally, or alternatively, optical filter coating portion 510 may be associated with a thickness of less than 100 μm, less than 50 μm, less than 10 μm, and/or the like.

In some implementations, a layer may be associated with multiple different thicknesses. For example, to form a set of channels, a thickness of a particular layer (e.g., a spacer layer disposed between a set of quarterwave stack reflectors formed by layers 530 and layers 540) may be varied to cause different wavelengths of light to be directed to different sensor elements of a sensor element array via different channels. In this way, a sensor window may enable use of a multispectral sensor to determine information regarding multiple wavelengths of light and to perform multiple sensing functionalities. In some implementations, optical filter 500 may form at least 32 channels, at least 64 channels, at least 128 channels, and/or the like to enable sensing of a threshold quantity of wavelengths. In some implementations, multiple channels may be associated with a common wavelength (e.g., one common wavelength, at least one common wavelength, and/or the like) for sensing by at least one sensor element aligned to the multiple channels.

In some implementations, optical filter 500 may be associated with a particular spectral range, such as a near-infrared spectral range, a mid-infrared spectral range, and/or the like. For example, optical filter 500 may be associated with a spectral range from approximately 600 nm to approximately 2500 nm, from approximately 600 nm to approximately 1100 nm, from approximately 700 nm to approximately 2000 nm, from approximately 900 nm to approximately 1500 nm, and/or the like. In some implementations, optical filter 500 may be associated with a particular channel separation, such as a channel separation of less than approximately 50 nm, less than approximately 20 nm, less than approximately 10 nm, less than approximately 5 nm, less than approximately 1 nm, and/or the like.

In some implementations, optical filter 500 may be associated with a threshold transmissivity, such as greater than approximately 50% transmissivity, greater than approximately 80% transmissivity, greater than approximately 90% transmissivity, greater than approximately 95% transmissivity, greater than approximately 99% transmissivity, and/or the like for a particular spectral range (e.g., a sensing spectral range). In some implementations, optical filter 500 may be associated with a threshold opacity (e.g., based on reflectance, absorption, and/or the like). For example, optical filter 500 may be associated with an opacity of greater than approximately 50% transmissivity, greater than approximately 80% transmissivity, greater than approximately 90% transmissivity, greater than approximately 95% transmissivity, greater than approximately 99% transmissivity, and/or the like for a particular spectral range (e.g., a visible spectral range). In this way, optical filter 500 enables color-selectivity for a sensor window and enables sensing by a sensor element disposed in an optical path of the sensor window.

As indicated above, FIG. 5 is provided as an example. Other examples may differ from what is described with regard to FIG. 5.

In this way, a user device may include a single, multispectral sensor device aligned to a multispectral filter to provide multiple sensing functionalities, such as biometric authentication sensing, health parameter monitoring sensing, and/or the like. Based on providing multiple sensing functionalities using a single, multispectral sensor device, the user device may be associated with reduced cost, reduced size, reduced complexity, reduced utilization of power resources, reduced utilization of network resources, and/or the like. Moreover, based on performing biometric authentication using subcutaneous spectroscopic measurements, the sensor device improves an accuracy of biometric authentication by obviating an effect of surface damage to a finger, dirt on a finger, water on a finger, and/or the like, and by using liveness detection to prevent an artificial imprint of a finger from being used in place of the finger.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term "component" is intended to be broadly construed as hardware, firmware, or a combination of hardware and software.

Some implementations are described herein in connection with thresholds. As used herein, satisfying a threshold may, depending on the context, refer to a value being greater than the threshold, more than the threshold, higher than the threshold, greater than or equal to the threshold, less than the threshold, fewer than the threshold, lower than the threshold, less than or equal to the threshold, equal to the threshold, and/or the like.

Certain user interfaces have been described herein and/or shown in the figures. A user interface may include a graphical user interface, a non-graphical user interface, a text-based user interface, or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, and/or the like). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related items, and unrelated items, etc.), and may be used interchangeably with "one or more." Where only one item is intended, the term "only one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A system for a user device, comprising:
 a single sensor device configured to perform a health monitoring functionality and a security functionality; and
 an optical filter comprising a plurality of layers,
  wherein thicknesses of the plurality of layers cause different wavelengths of light to be directed to different sensor elements of the single sensor device,
  wherein the single sensor device is a single multispectral sensor configured to perform the health monitoring functionality and the security functionality based on the different wavelengths of light,
  wherein, to perform the security functionality, the single sensor device is configured to:
   perform the security functionality using a subcutaneous identification technique, and
  wherein, to perform the health monitoring functionality, the single sensor device is configured to:
   perform the health monitoring functionality based on measurements of one or more wavelengths of light reflected.

2. The system of claim 1, further comprising:
a sensor window that is opaque in a visible spectral range and transmissive in a sensing spectral range.

3. The system of claim 2, wherein the sensing spectral range is a near-infrared spectral range or a mid-infrared spectral range.

4. The system of claim 1, further comprising:
a sensor window configured to be a particular color, in a visible spectral range, that matches an adjacent surface of the user device and conceals the single sensor device.

5. The system of claim 1, further comprising:
a sensor window configured to protect the single sensor device from an external environment.

6. The system of claim 1, wherein, to perform the security functionality using the subcutaneous identification technique, the single sensor device is configured to:
transmit near-infrared light through a sensor window; and
determine a biometric authentication based on a tissue structure in a finger of a hand.

7. The system of claim 6, wherein, to determine the biometric authentication, the single sensor device is configured to:
receive a portion of the near-infrared light reflected off one or more of capillaries or veins in the finger;
determine a vascular structure in the finger based on receiving the portion of the near-infrared light; and
determine the biometric authentication based on the vascular structure,
wherein the tissue structure is the vascular structure.

8. The system of claim 1, wherein the subcutaneous identification technique comprises sensing to a penetration depth of greater than 0.1 microns.

9. The system of claim 1, wherein the single sensor device is further configured to perform a spectroscopic classification or quantification using measurements of near-infrared light.

10. The system of claim 1, wherein the single sensor device is further configured to:
provide, based on performing the security functionality and performing the health monitoring functionality, information indicating that a fingerprint was from a person and not an artificial imprint.

11. A method, comprising:
performing, by a single sensor device that is one of a plurality of components of a user device, a security functionality using a subcutaneous identification technique based on one or more first wavelengths of light received at the single sensor device,
wherein the user device comprises an optical filter comprising a plurality of layers, and
wherein thicknesses of the plurality of layers cause different wavelengths of light to be directed to different sensor elements of the single sensor device;
transmitting, by the single sensor device, a near-infrared light toward a hand of a user;
receiving, by the single sensor device, reflected light based on transmitting near-infrared light toward the hand; and
detecting, by the single sensor device, a health parameter of the user based on measurements of one or more second wavelengths of the reflected light.

12. The method of claim 11, wherein the health parameter is a heart rate.

13. The method of claim 11, further comprising:
performing a liveness determination based on the health parameter; and
automatically unlocking a user interface of the user device, associated with the single sensor device, based on performing the security functionality and the liveness determination.

14. The method of claim 11, further comprising:
automatically altering a layout of a screen or one or more preferences of the user device, associated with the single sensor device, based on performing the security functionality and a liveness determination.

15. The system of claim 1, wherein the subcutaneous identification technique comprises sensing to a penetration depth of greater than 5 microns.

16. A user device, comprising:
a display;
a single sensor device disposed behind the display and configured to perform multiple different sensing functionalities,
wherein the multiple different sensing functionalities include one or more of:
a security functionality,
a health monitoring functionality, or
a liveness determination; and
an optical filter comprising a plurality of layers,
wherein thicknesses of the plurality of layers cause different wavelengths of light to be directed to different sensor elements of the single sensor device, and
wherein the single sensor device is configured to perform the multiple different sensing functionalities based on the different wavelengths of light.

17. The user device of claim 16, wherein, to perform the multiple different sensing functionalities, the single sensor device is configured to:
perform the security functionality using a subcutaneous identification technique.

18. The user device of claim 16, wherein, to perform the multiple different sensing functionalities, the single sensor device is configured to:
perform the health monitoring functionality based on measurements of one or more wavelengths of light reflected from a hand.

19. The user device of claim 16, wherein, to perform the multiple different sensing functionalities, the single sensor device is configured to:
perform the liveness determination based on a heart rate.

20. The user device of claim 16, wherein the display is configured to provide, for display and based on the liveness determination, information that indicates that liveness is confirmed.

* * * * *